United States Patent [19]
Colbert

[11] 4,373,914
[45] Feb. 15, 1983

[54] ORTHODONTIC DEVICE

[76] Inventor: Earl J. Colbert, 3696 Montego Dr., Huntington Beach, Calif. 92649

[21] Appl. No.: 316,764

[22] Filed: Oct. 30, 1981

[51] Int. Cl.³ ............................................... A61C 7/00
[52] U.S. Cl. ...................................................... 433/18
[58] Field of Search ............................. 433/18, 2, 22

[56] References Cited
U.S. PATENT DOCUMENTS
3,879,850  4/1975  Wallshein ............................. 433/18

Primary Examiner—Robert Peshock
Attorney, Agent, or Firm—Lawrence L. Colbert

[57] ABSTRACT

Orthodontic device used to rotate teeth back to their normal position by using a compressible rubber device in combination with the usual brackets and wires.

3 Claims, 5 Drawing Figures

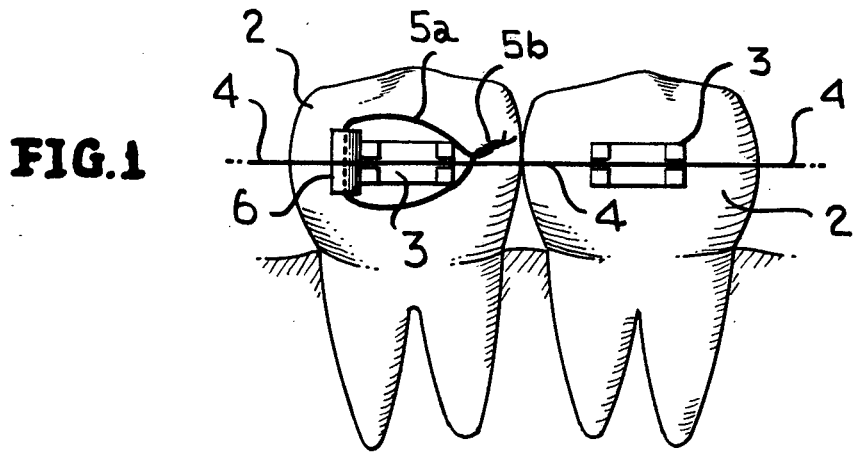
FIG.1
FIG.2
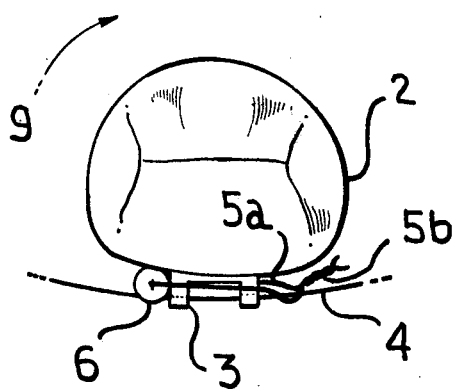
FIG.5
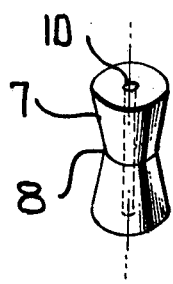
FIG.3
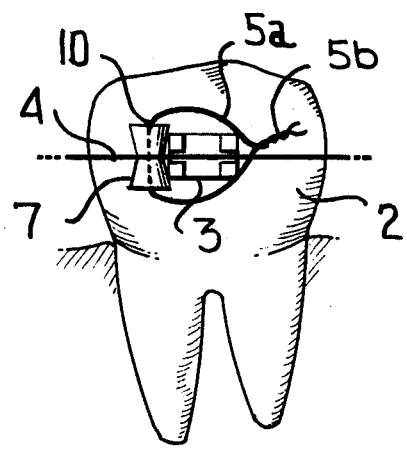
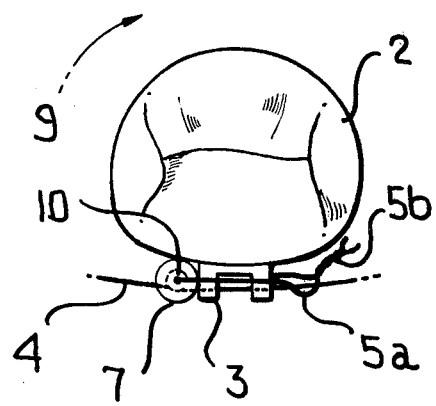
FIG.4

ORTHODONTIC DEVICE

BACKGROUND AND SUMMARY OF THE INVENTION

In the orthodontic profession teeth are manipulated by various devices in order for the teeth to return to their normal position. This is for cosmetic reasons and also so that the patient maintains proper bite between their lower and upper teeth.

If teeth are off line they can cause headache of varied intensity and improper mastication of food both of which can be cured by proper alignment by proper application of devices consisting mainly of brackets and wires by skilled orthontists.

Known prior are U.S. Pat. Nos. 3,913,228, 4,054,997 and 3,879,850. Also known manufactured devices which are a spring wedge which is known as Steiner Rotation Spring Wedge and Alastic Rotation Wedge, one of which shows structure similar to that disclosed by this invention.

OBJECTS OF THE INVENTION

It is an object of the invention to provide an improved orthodontic auxiliary device.

Another object of the invention is to provide an orthodontic device that is simple in construction, economical to manufacture and efficient to use.

With the above and other objects in view, the present invention consists of the combination and arrangement of parts hereinafter more fully described, illustrated in the accompanying drawing and more particularly pointed out in the appended claims, it being understood that changes may be made in the form, size, proportions and minor details of construction without departing from the spirit or sacrificing any of the advantages of the invention.

DESCRIPTION OF DRAWINGS

FIG. 1 is a side elevational view of a basic form of the invention as applied to teeth to be straightened;

FIG. 2 is a top plan view thereof only showing application to one tooth;

FIG. 3 is a side elevational view of the preferred form of the invention;

FIG. 4 is a top plan view of FIG. 3; and

FIG. 5 is a perspective view of the rotator.

DETAILED DESCRIPTION

Now with more particular reference to the drawings, teeth generally indicated at 2 to which are applied orthodontic brackets 3 in the normal manner against which and attached to the brackets is an arch wire 4. In order to cause a tooth to move in the direction indicated by arrow 9 rotators 6 and 7 are used. These rotators are in two forms like 6 which is rod shaped and 7 which has a rod shape but with a central circumferential recess 8 or hour glass shape or which can be described as a rod with a central recess and for which I claim invention. These rotators are made of compressible rubber like material through which a ligature wire 5a is centrally disposed at 10 with the opposite ends of the wire twisted as at 5b to hold it secure in relation to the arch wire 4 and bracket 3 and to compress the rotator.

The central recess 8 of rotator 7 rests against the arch wire 4 and is held more secure and locked in position preventing it from slipping out from under the arch wire as would be the case if a plain rod shape was used.

As otherwise expressed the rotator is recessed so that it centers itself under the arch wire 4 and has less tendency to slip out from between the wire and tooth. The plain rod type does not maintain itself in the center.

The rotator is wedged between the arch wire 4 and tooth next to bracket causing it to compress with ligature wire 5a holding the rotator securely in this position. When the rubber rebounds it puts pressure against the arch wire and tooth, with the tooth reacting to pressure and moves in the direction of arrow 9.

Having described the invention it is to be understood that the above described is the preferred form of the invention. Numerous other arrangements of the invention may be made by those skilled in the art without departing from the spirit and scope of the invention.

I claim:

1. An orthodontic device comprising a bracket connected to a tooth, an arch wire associated with said bracket, a rod shaped rotator with a ligature wire for attaching said rotator and connecting the rotator adjacent said bracket and between said arch wire for holding said rotator securely for permitting rotation of the tooth.

2. An orthodontic device as defined in claim 1 having a rotator wich has a circumferential depression.

3. An orthodontic device as defined in claim 2 having a rotator with a centrally located circumferential depression.

* * * * *